United States Patent
Lundberg et al.

(10) Patent No.: US 8,146,406 B2
(45) Date of Patent: Apr. 3, 2012

(54) VIBRATING TRANSMITTER FOR CONSISTENCY MEASUREMENT

(75) Inventors: Peter Lundberg, Åmål (SE); Joakim Kullander, Säffle (SE)

(73) Assignee: BTG Pulp & Paper Sensors AB, Saffle (SE)

( * ) Notice: Subject to any disclaimer, the term of this patent is extended or adjusted under 35 U.S.C. 154(b) by 861 days.

(21) Appl. No.: 12/093,330

(22) PCT Filed: Oct. 30, 2006

(86) PCT No.: PCT/SE2006/001220
§ 371 (c)(1),
(2), (4) Date: Sep. 22, 2008

(87) PCT Pub. No.: WO2007/055633
PCT Pub. Date: May 18, 2007

(65) Prior Publication Data
US 2011/0162440 A1  Jul. 7, 2011

(30) Foreign Application Priority Data
Nov. 14, 2005  (SE) .................................. 0502501-0

(51) Int. Cl.
*G01N 15/06* (2006.01)
(52) U.S. Cl. ...................... 73/53.03; 73/53.01; 73/61.75
(58) Field of Classification Search .................. 73/53.03, 73/54.01
See application file for complete search history.

(56) References Cited

U.S. PATENT DOCUMENTS

| | | | | |
|---|---|---|---|---|
| 4,677,846 A | * | 7/1987 | Lundberg | 73/53.03 |
| 4,822,249 A | * | 4/1989 | Eckardt et al. | 416/235 |
| 5,349,848 A | | 9/1994 | Driver | |
| 5,369,987 A | * | 12/1994 | Nettamo et al. | 73/54.23 |

FOREIGN PATENT DOCUMENTS

| | | |
|---|---|---|
| EP | 0 992 766 A1 | 4/2000 |
| WO | 85/04716 A1 | 10/1985 |
| WO | 98/38477 A1 | 9/1998 |

* cited by examiner

*Primary Examiner* — Hezron E Williams
*Assistant Examiner* — Gregory J Redmann
(74) *Attorney, Agent, or Firm* — Young & Thompson

(57) ABSTRACT

The invention relates to a transmitter for consistency measuring of pulp suspensions at first hand, comprising a measuring body (1), shaped such as a blade, suspended in a vibration-producing apparatus. The measuring body (1) shaped such as blade (1') shows wave-shaped side surfaces (9, 10) in its transverse direction and is vibratable in a frequency of oscillation between 20-80 Hz and with a predetermined amplitude of +/−2-8 mm, that provides a combination of both shearing force measurement and a measurement of the resistance of conveyance of liquid through a fiber netting.

3 Claims, 4 Drawing Sheets

VIBRATING TRANSMITTER FOR CONSISTENCY MEASUREMENT

Figure 1:
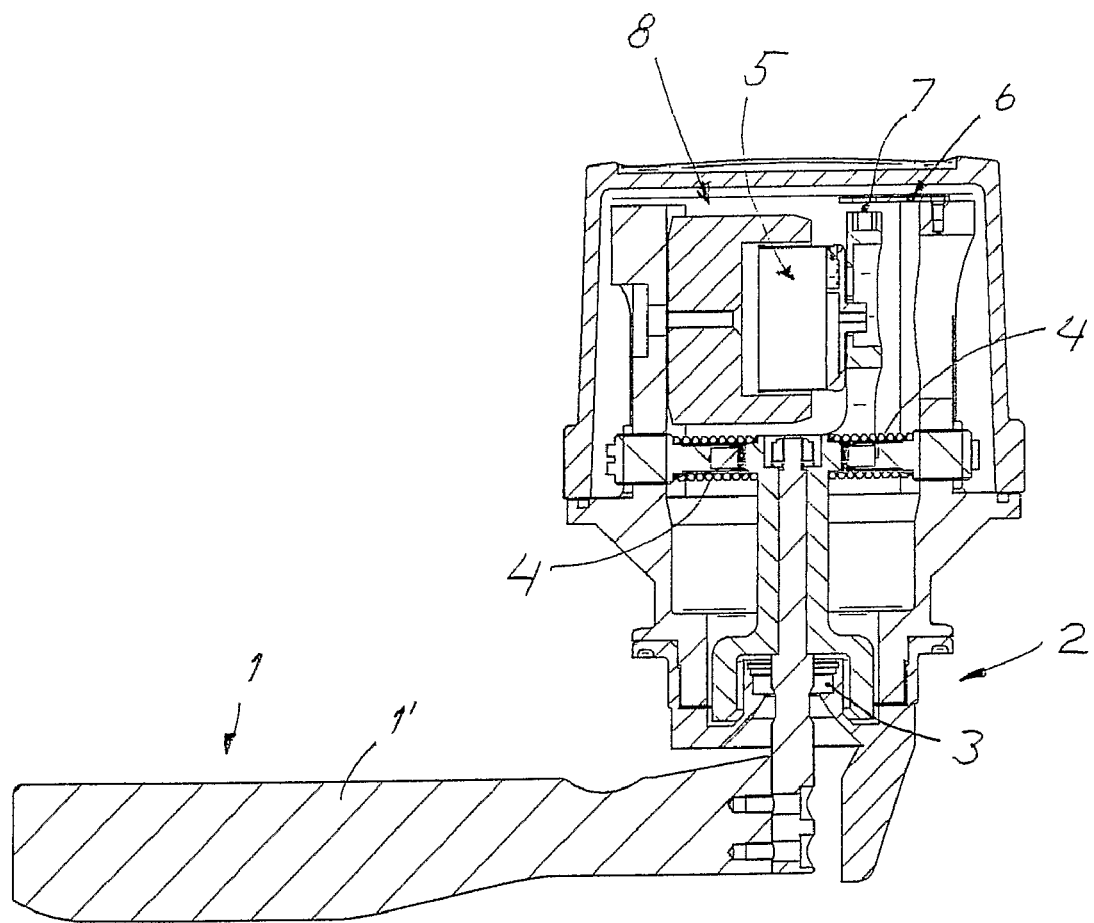

The present invention relates to a vibrating transmitter for consistency measurement of first of all pulp suspensions.

There are today a number of different measuring principles for fibre consistency measurement. The most frequent occurring are rotating shearing force meters (rotating measuring body), optical transmitters for transmission measurement and reflection measurement, respectively, microwave meters and also static and active blade transmitters for shearing force measurement (measuring body in the form of a blade in the longitudinal direction of the process conduit). The three first mention types are usually used for more demanding applications and also commands a higher price than the last mentioned blade transmitters, that traditionally are used in less demanding applications.

Within e.g. the recycled fibre handling, that in a global view has increased very heavily during the last years, new problems have appeared, and that, in its turn, requires new demands on measuring transmitters. The content of the suspensions of prime fibres, recycled fibres, fine fractions, filler etc. varies considerably and most apparent are the relatively low shearing force levels, that are retrieved in many applications. But here, as in processes where recycled fibres are not present, there are a number of application spots that are considered less qualified and thus does not justify installation of transmitters in the upper price range. The problems with the lower shearing force levels becomes of course most apparent in low consistency areas. As a result of this, installations of blade transmitters, as well as static and active, have obvious problems with the sensitivity in the consistency range 1-4% and sometimes still higher up in the range. Below 1%, a blade transmitter has usually none or very slight sensitivity and in this case are optical transmitters used. In upper consistency areas, 4% and over, one chooses transmitters on basis of demand of the application for sensitivity and accuracy of measurement, and the selection then becomes fairly large and might principally comprise all of the above types.

Vibrating measuring transmitters are in itself not a new phenomenon. For mere viscosimetric measurements, over the years, a number of such apparatuses has been designed and applied for by patent applications. In this case the measuring principle has provided fine results and obtained a given position in the processing industry. However, when during the seventies, one tried to transfer the fine results to shearing force meters of blade transmitter type in the paper and pulp industry, problems occurred that one had not expected and the measuring principle is not used today in fibre consistency meters. One of the problems were caused by the high vibration frequency used, one other by the design of the measuring body (the blade).

The relatively high measuring frequency caused the stroke (amplitude) of the blade to become considerably limited and one were setting the amplitude to 0.1-1 mm, which is not sufficient considering the water film that is formed at the surfaces of the blade, during certain conditions, which can be many times larger. One had knowledge of possible origin of water film and the sides of the blade were designed with longitudinal extending borders, but during certain conditions the borders still contributed to the formation of water film and the measuring result was jeopardized.

During the eighties, a further active blade transmitter principle was introduced, where the measuring body provides strokes through the netting of fibres at intervals of a couple of seconds. The principle is used successfully still today, but has the previous mentioned problems in the low consistency area and, in that case, especially within the recycled fibre handling.

One object with the present invention is to provide the market with a transmitter that, without command a price in the upper part of the scale, in a satisfactory way manage to perform consistency measurements in recycled fibre applications in the range 1-4%. It is obvious that a transmitter according to the invention also obtains good performances in other applications outside the area of recycled fibres and outside said consistency area.

Yet one object with the present invention is to minimise the difference in output signal for a given pulp consistency in suspensions with varying and partly unknown composition. The characteristic features of the present invention are defined in the following claims.

Figure 2:
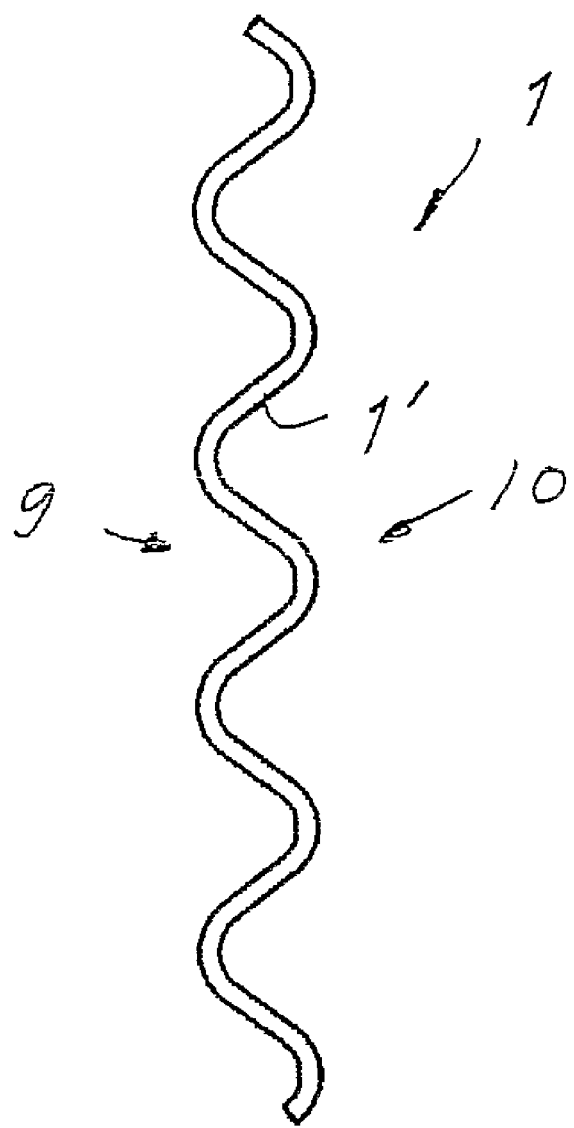
Figure 3:
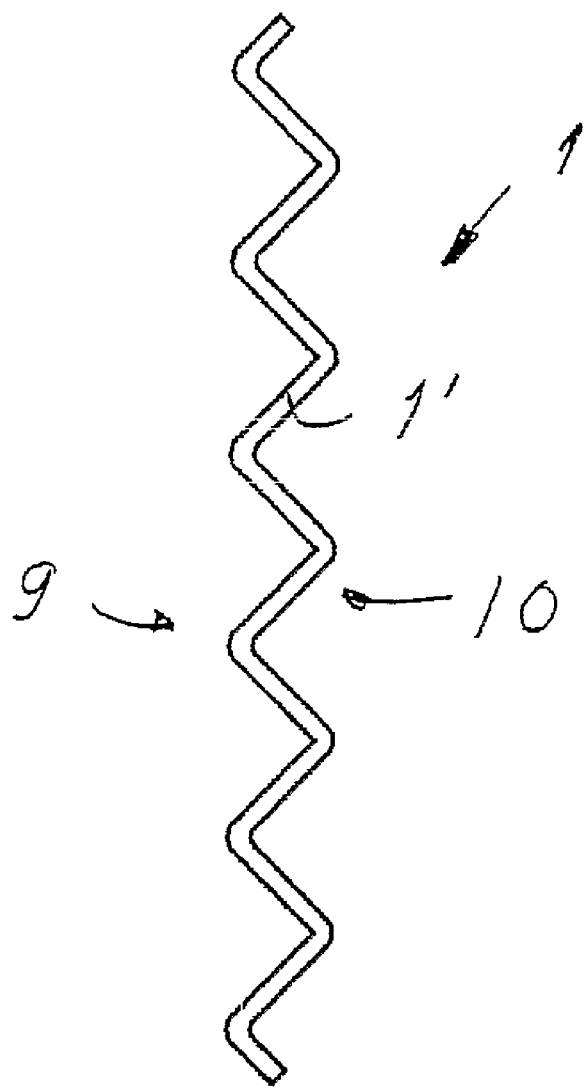
Figure 4:
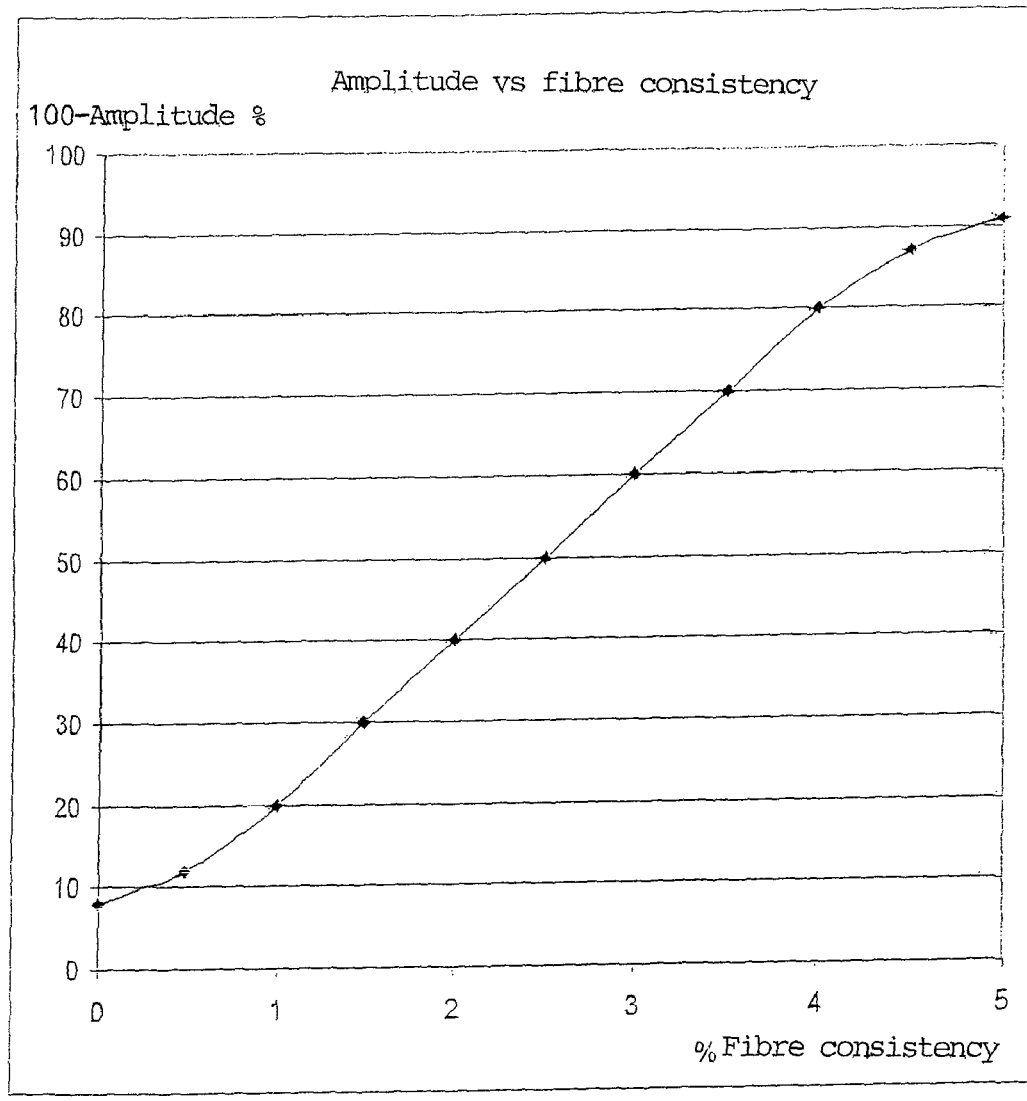

The invention is described more in detail by assistance of preferred embodiments by reference to the attached drawings, in which FIG. 1 shows a cross-section of a transmitter according to the present invention that has a measuring body in the shape of a blade, FIG. 2 shows a section in transverse direction of a first embodiment of a measuring body in the shape of a blade, which sides are wave-shaped with rounded-off wave crests and wave troughs, FIG. 3 shows a section in transverse direction of an alternative embodiment of a measuring body in the shape of a blade, that shows a wave formation with tip-shaped wave crests and wave troughs, and FIG. 4 shows a graph of how an oscillating amplitude of a measuring body agrees with the present fibre consistency.

The invention is based on that a measuring body oscillates with a fast frequency in a suspension, whereby the oscillating amplitude will vary depending on the fibre consistency of the suspension. The amplitude will be a reversed function of the fibre consistency and might after signal processing be calculated and presented as an output signal of the measured consistency.

As illustrated in FIG. 1, a measuring body 1, introduced in the suspension, in the shape of a blade 1', that is suspended in a bearing system 2 and an elastic sealing member 3, and that further is positioned by an opposite spring system 4 and an excitation system with a coil and magnet 5, is brought to oscillate with a fixed applied sinusoidal current from an electric operating device 6, in a typical self-resonance range of 30-60 Hz for the apparatus. The amplitude is measured with a linear position detecting sensor 7, and is calculated and presented as an electrical output signal in an electronic unit 8. The present oscillating motion is +/−5 mm and maximally +/−8 mm in pure water and decreases with increasing pulp consistency. At a certain consistency, the oscillating motion becomes too little to ensure that an occurring water film is broken, and in order to avoid that, the transmitter can be provided with blades in different sizes for different consistency areas. Two examples of embodiments of blades for a measuring body is shown in FIGS. 2 and 3 and the wave-shaped sides 9 and 10 provides an effective result with a pulsating conveyance of liquid through the suspension. The wave-formation that the blade 1' according to the first embodiment shows is evident from FIG. 2 and according to this, the blade has a sinusoidal cross-section with well rounded-off wave crests and wave troughs, while for the one shown in the embodiment in FIG. 3, the blade has in cross-section saw-tooth shaped tip-formations with only slightly rounded-off wave crests and wave troughs.

The shape of the vibrating measuring body 1 and also the amplitude in the present invention admits a combination of a shearing force measuring and a measurement of the resistance of the conveyance of liquid through fibre netting. A relatively large amplitude guarantees that upper and lower borders of the measuring body always cuts through the fibre netting and not solely through the water film that often covers the measuring body. The wave-shaped sides 9 and 10 of the measuring body 1, according to FIGS. 2 and 3, provides for said pulsating conveyance of liquid through the fibre netting/suspension. There are also other forces that influence the measuring, but the two mentioned above are those that have greatest influence.

For long-fibred pure pulp qualities the shearing force is large, while the liquid conveyance through the netting takes place at a relatively low resistance. For e.g. recycled fibre suspensions, on the other hand, the condition is inverse. Filler, fine fraction, recycled fibres and the lower amount prime fibres, provides a low shearing force but a high resistance against water conveyance through the netting. On basis of measurement, the consequence will be that the difference in output signal, for a given consistency and varying pulp quality, will become considerable less than for other blade transmitters. This is an obvious advantage for the users, that to a less extent need to re-calibrate the transmitters at shifting of quality. Sometimes this is not even possible, since the composition of the pulp may vary in an unknown way depending on raw material and season.

According to the invention, the measuring body 1 is brought to oscillate at its natural frequency with constant supplied force and frequency of the oscillation. The measuring of the oscillating amplitude provides the advantage that the sensitivity is highest at low fibre consistency and lowest at high fibre consistency, which in turn result in that one, due to that shearing force has an inverse sensitivity curve, receives a more linear measuring signal, see FIG. 4, without mathematical adjustment of the shape of the curve. Usually, a suitable frequency is between 30-60 Hz and an oscillating amplitude is +/−5 mm. The correct choice of amplitude and frequency has large significance in order for maximal transportation of liquid to occur through the netting, without occurrence of bubble formation, due to pulsating pressure drops that releases oxygen, to come up at the surface of the measuring body 1. In extreme cases, the frequency can be between 20-80 Hz and the amplitudes starting value in water can be +/−8 mm.

In the graph according to FIG. 4 is shown, as an example, the inverted value of the amplitude as a function of fibre consistency. The highest sensitivity is between about 1% to 4% fibre consistency. If the value of the amplitude in water in the example shown is +/−5 mm, the amplitude consequently becomes about +/−4.5 mm at 1% consistency and about +/−0.5 mm at 4% consistency. In the example it would not be suitable to provide the transmitter a larger measuring range, since the measuring should be jeopardized by water film at consistencies above 4% and also of the low sensitivity below about 1%.

The invention claimed is:

1. A transmitter for consistency measuring of pulp suspensions, comprising:
    a measuring body, shaped as a blade, suspended in a vibration-producing apparatus; and
    a linear position detecting sensor configured to measure an amplitude of the measuring body,
    wherein the measuring body shaped as the blade shows wave-shaped side surfaces in a transverse direction,
    wherein in a cross-section the wave-shaped side surfaces show one of:
        i) a sinusoidal wave-shape with rounded-off with longitudinal wave crests and wave troughs and
        ii) a wave-shape with saw-tooth shaped with rounded-off wave crests and wave troughs, and
    wherein the measuring body is configured to vibrate at a natural frequency of oscillation between 20-80 Hz and with the amplitude of +/−2-8 mm, the linear position detecting sensor measures the amplitude as a combination of both shearing force measurement and a measurement of the resistance of conveyance of liquid through a fiber netting.

2. The transmitter according to claim 1, wherein the measuring body is intended to vibrate or oscillate in a preferred frequency between 30-60 Hz and an oscillating amplitude of +/−5 mm.

3. The transmitter according to claim 1, further comprising:
    the measuring body that is suspended in a bearing system and an elastic sealing member, and that simultaneously is positioned by an opposite spring system and an excitation system with a coil and magnet to oscillate with a fixed applied sinusoidal current from an electric operating device, in a typical self-resonance range of 30-60 Hz for the apparatus.

* * * * *